United States Patent [19]

Snook et al.

[11] Patent Number: 4,594,533
[45] Date of Patent: * Jun. 10, 1986

[54] DEVICE FOR ANALYZING CHEMICAL SUBSTANCE

[75] Inventors: Martin Snook, Harrow; James M. Rideout, Sanderstead; Alan Renshaw, Chesham, all of England

[73] Assignee: National Research Development Corp., London, England

[*] Notice: The portion of the term of this patent subsequent to May 11, 1999 has been disclaimed.

[21] Appl. No.: 675,464

[22] Filed: Nov. 28, 1984

Related U.S. Application Data

[63] Continuation of Ser. No. 312,167, Oct. 10, 1981, abandoned, which is a continuation of Ser. No. 48,775, Jun. 15, 1979, Pat. No. 4,329,061, which is a continuation of Ser. No. 748,405, Dec. 8, 1976, abandoned, which is a continuation of Ser. No. 567,406, Apr. 11, 1975, abandoned, which is a continuation-in-part of Ser. No. 467,796, May 7, 1974, abandoned.

[30] Foreign Application Priority Data

May 8, 1973 [GB] United Kingdom ............. 21935/73
Feb. 4, 1975 [GB] United Kingdom ............. 4741/75
Feb. 4, 1975 [GB] United Kingdom ............. 4742/75

[51] Int. Cl.[4] .................................... H05B 37/00
[52] U.S. Cl. ............................ 315/363; 250/576; 356/414; 356/440
[58] Field of Search ................ 356/39–41, 356/409, 414, 418, 432, 440; 250/576; 315/363

[56] References Cited

U.S. PATENT DOCUMENTS

| | | | |
|---|---|---|---|
| 3,193,358 | 7/1965 | Baruch | 23/230 R |
| 3,322,956 | 5/1967 | Shah | 250/224 X |
| 3,503,683 | 3/1970 | Isreeli et al. | 356/36 |
| 3,504,981 | 4/1970 | Malvin | 356/425 X |
| 3,555,284 | 1/1971 | Anderson | 250/565 |
| 3,567,393 | 3/1971 | Welch | 356/39 X |
| 3,576,441 | 4/1971 | Adams | 250/564 |
| 3,589,867 | 6/1971 | Heinz et al. | 23/230 R |
| 3,656,116 | 4/1972 | Jansen | 250/573 |
| 3,697,185 | 10/1972 | Kassel et al. | 356/418 |
| 3,743,426 | 7/1973 | Steinberg | 356/418 |
| 3,748,044 | 7/1973 | Liston | 356/409 |
| 3,798,459 | 3/1974 | Anderson et al. | 250/576 |
| 3,829,221 | 8/1974 | de Mendez et al. | 356/409 X |
| 3,834,821 | 9/1974 | Ferrari et al. | 356/246 X |
| 3,861,809 | 1/1975 | Hall, Jr. | 356/418 |

FOREIGN PATENT DOCUMENTS

| | | |
|---|---|---|
| 0100823 | 4/1937 | Australia . |
| 2020711 | 11/1971 | Fed. Rep. of Germany . |
| 47-41776 | 12/1972 | Japan . |
| 0513393 | 11/1971 | Switzerland . |
| 0977829 | 12/1964 | United Kingdom . |
| 1075152 | 7/1967 | United Kingdom . |
| 1137867 | 12/1968 | United Kingdom . |
| 1176747 | 1/1970 | United Kingdom . |
| 1189840 | 4/1970 | United Kingdom . |
| 1244744 | 9/1971 | United Kingdom . |
| 1250218 | 10/1971 | United Kingdom . |
| 1318984 | 5/1973 | United Kingdom . |
| 1320718 | 6/1973 | United Kingdom . |

OTHER PUBLICATIONS

*The Role of a Multichannel Analyzer in Clinical Chemistry*, British Clinical Laboratory Equipment (M. A. Buttolph, Ed.) G.O.I. London (1972) pp. 16–19.

Pardue et al., *Multichannel Analyzer Featuring Ultrahigh Stability Photometry*, Clinical Chemistry, vol. 18, No. 9, 1972, pp. 928–933.

(List continued on next page.)

*Primary Examiner*—David K. Moore
*Attorney, Agent, or Firm*—Cushman, Darby & Cushman

[57] ABSTRACT

The present invention concerns a device for analyzing chemical substances and monitoring chemical reactions in which cuvettes on a turntable are rapidly scanned by light at test and reference wavelengths and intensity of the light after passage through the cuvettes monitored by a photodetector. The output of the photodetector is logically processed so that measurements can be made of the varying optical densities in the samples scanned.

5 Claims, 11 Drawing Figures

OTHER PUBLICATIONS

Anderson, *Analytical Techniques for all Fractions, A Multiple-Level Rotor for a New Microanalytical System*, Analytical Biochemistry 28 (1969) pp. 545–562.

*Multichannel 300*, Biomedical Engineering, vol. 4, (1968) pp. 177–179.

Mitchell, *Vickers Multichannel/300 High Speed Analyzer*, reprint from Automated Multiphasic Health Testing, Engineering Foundation (1971) pp. 134–141.

Fisher Catalog 70, pp. 234–236.

"Clinical Chemistry", vol. 9, No. 5, Oct. 1963.

Hatcher "Rapid Automated Analyses Performed in Parallel", Clinical Chemistry, vol. 17, No. 6, 1971, pp. 475–480.

Cho et al., "Biomedical Instrumentation", Oak Ridge Recorder, May 1971.

"Clinical Laboratory Forum", Eli Lilly & Co., vol. 2, No. 7 1970, pp. 1 et seq.

DEVICE FOR ANALYZING CHEMICAL SUBSTANCE

This application is a continuation of our application Ser. No. 312,167 filed Oct. 10, 1981, now abandoned, which is a continuation of Ser. No. 48,775, filed June 15, 1979 now U.S. Pat. No. 4,329,061, which was a continuation of our continuation Ser. No. 748,405, filed Dec. 8, 1976, now abandoned, which was a continuation of our application Ser. No. 567,406, filed Apr. 11, 1975, now abandoned, which is continuation-in-part application Ser. No. 467,796, filed May 7, 1974, now abandoned.

The present invention concerns a device for the analysing of chemical substances or for use in monitoring chemical reactions, and is particularly, but not exclusively, concerned with the analysis of biochemical substances.

For example, clinical need has been established for accurate enzymo analysis, and the most acceptable type of this assay is based on the changes of absorbance when an enzyme kinetically reacts upon a substrate.

This type of analysis, which comprises a significant portion of the laboratory work load, is unsuitable for Continuous Flow Analysis, and attempts utilising Discrete Continuous, and Discrete Discontinuous systems have not been entirely successful.

For example, in known Discrete Continuous systems the throughput of specimens is determined by the time over which each reaction is separately followed. This is usually between one or two minutes, which results in only thirty or sixty specimens being processed per hour.

An alternative system has been proposed using a rotor carrying a batch of specimens or samples which are continuously monitored for changes in absorbance by rotating the rotor so that the samples pass in sequence through a static light beam. However, the loading of the specimen samples into this system is laborious and time consuming, i.e., all samples have to be placed in position on the rotor before analysis can start, and all have to be removed before a further batch can be analysed.

In accordance with one aspect of the present invention, there is provided a device for analysing chemical substances comprising a turntable having a plurality of positions where discrete samples to be analysed can be carried, means for indexing the turntable so that said positions are advanced past a loading station, means for sequentially directing light on to each of the said positions, and photosensitive means for measuring light from said source which has passed through one of said samples.

In accordance with another aspect of the present invention there is provided a device for use in monitoring chemical reactions, comprising a turntable having a series of sample holders arranged in a circular array centred on the axis of rotation of the turntable, means for repeatedly rotating the turntable intermittently as by indexing, or continuously at a slow pace, so that each sample holder will during one revolution successively pass through a location at which it can be loaded, a monitoring region and a location at which it can be unloaded, means for repeatedly scanning in sequence with a beam of light those sample holders disposed in said monitoring region, the scanning means being operative while the turntable is being rotated so that each sample holder is scanned many times during its passage through the monitoring region, and means for detecting light from said beam after it has passed through any sample in a sample holder located in said monitoring region.

It is to be understood that in this specification the term light includes ultra-violet and infra-red radiation as well as visible radiation.

Embodiments of the present invention will now be described by way of example and with reference to the accompanying drawings, in which:

FIG. 1 is a diagrammatic and partial cross-sectional view in elevation of a biochemical analyser particularly suited for enzyme analysis, FIG. 2 is a cross-section of part of the analyser of FIG. 1 showing a system for chopping light into alternating frequencies, FIG. 3 shows a cross-section through a second device for monitoring reactions constructed in accordance with the present invention, together with a diagrammatic representation of certain associated components;

Figure 1:
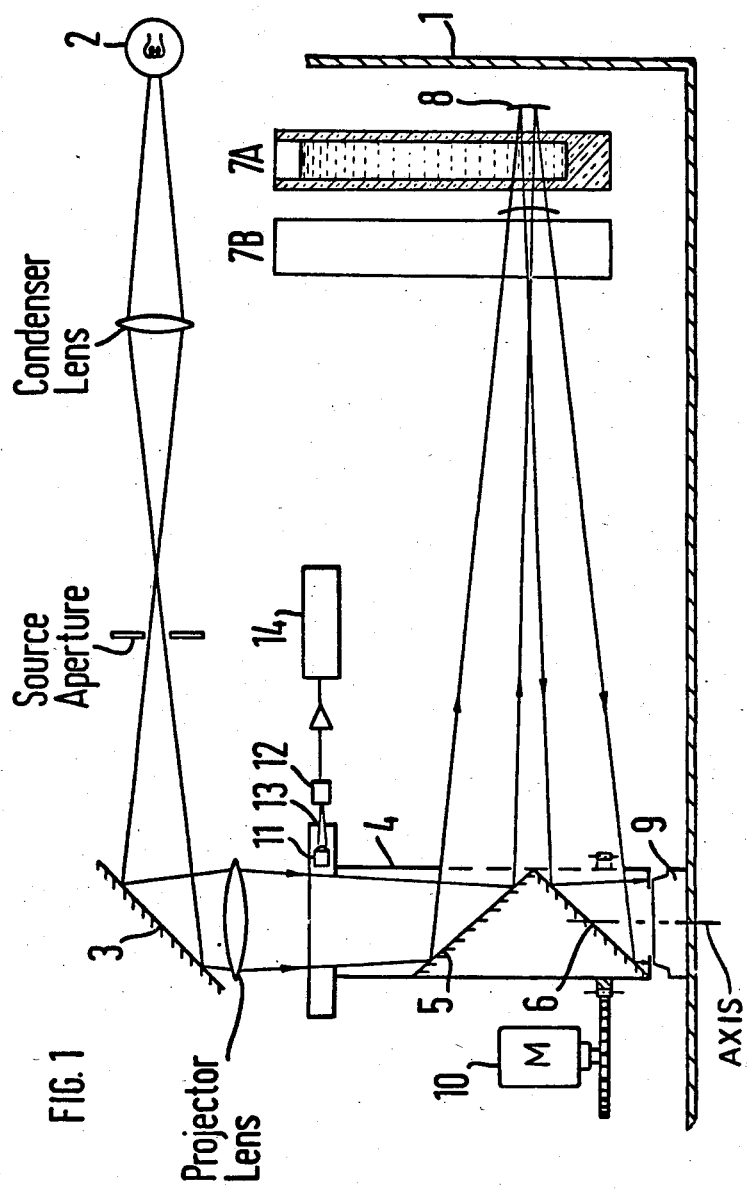
Figure 3:
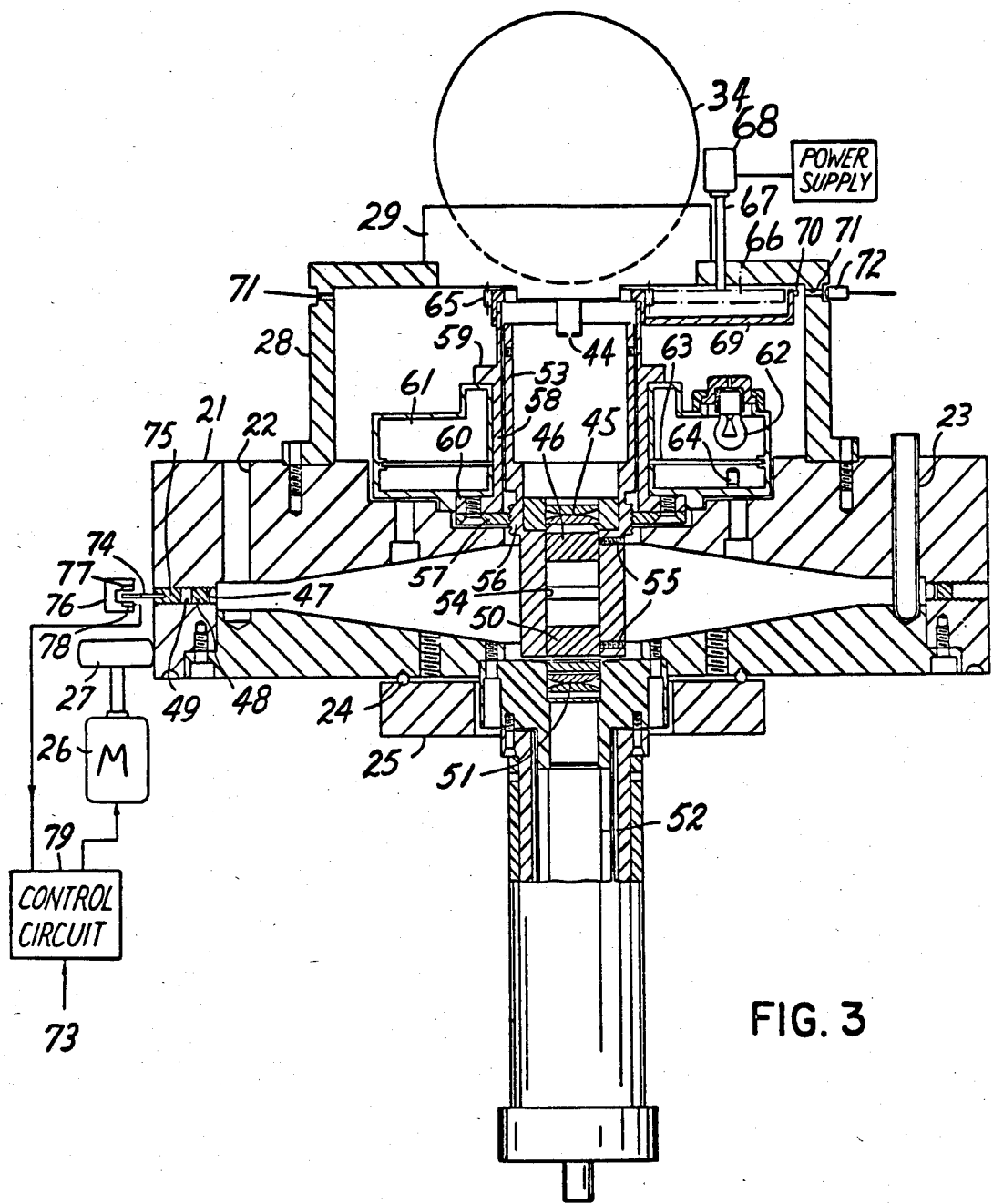
Figure 6:
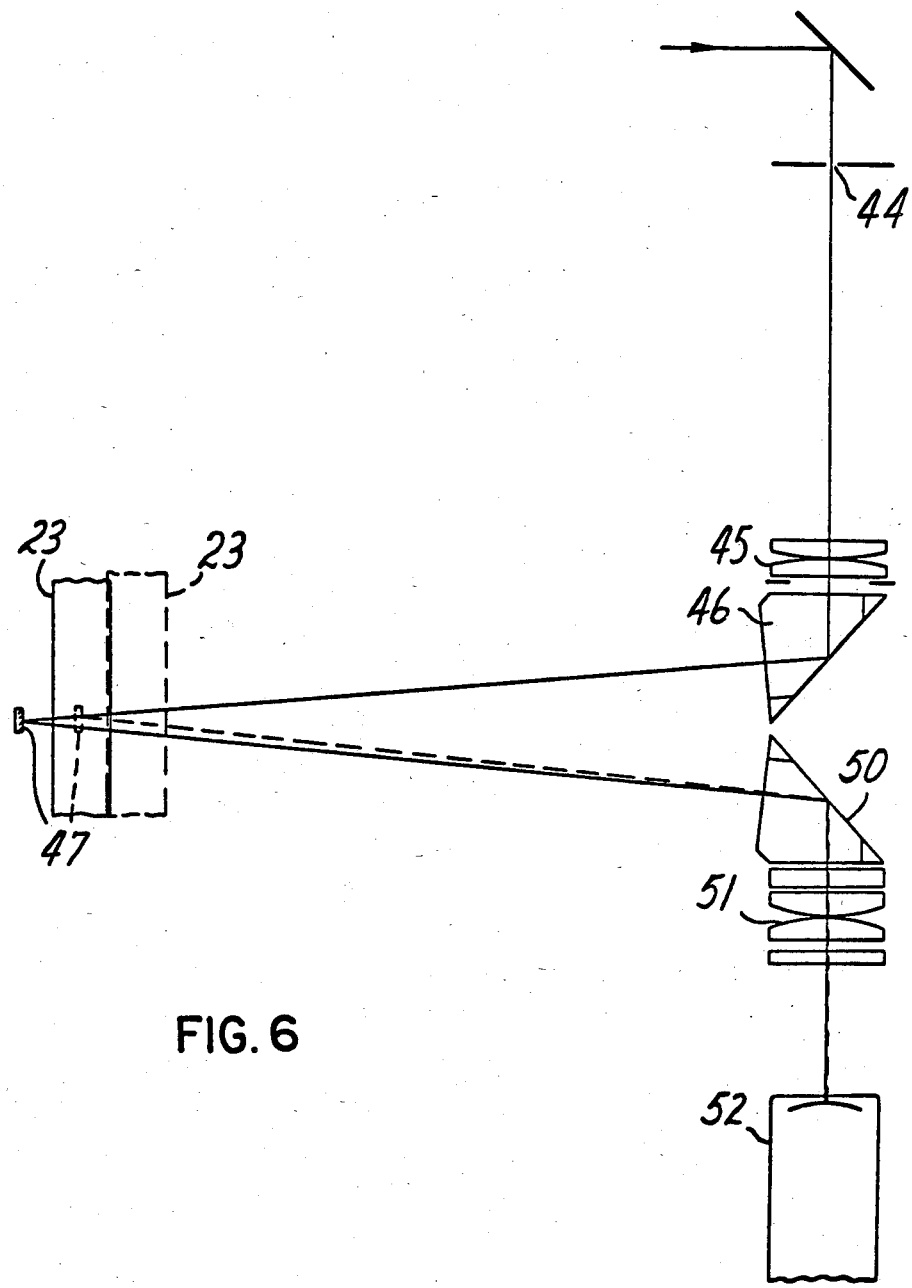
FIG. 6 is a diagrammatic view of the optical system of the device of FIG. 3.
Figure 7:
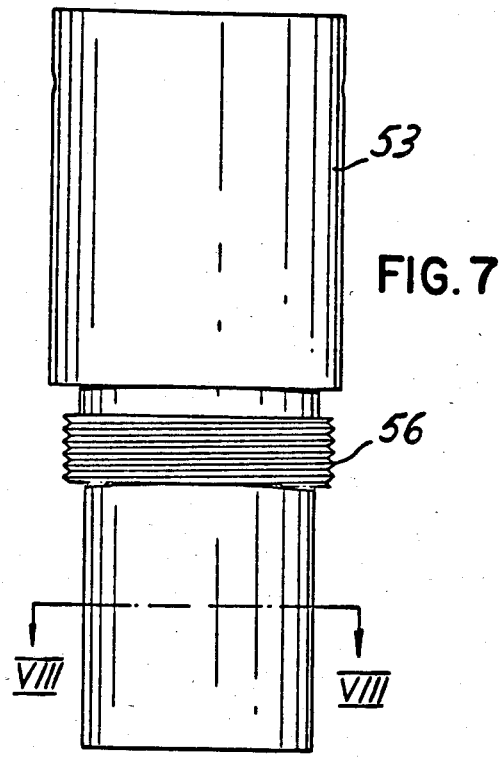
Figure 8:
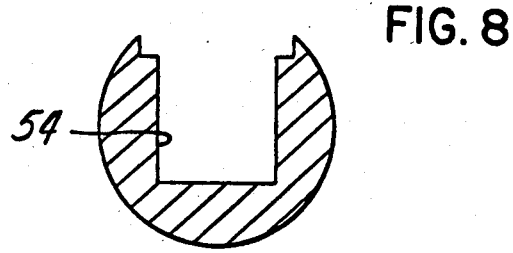
Figure 9:
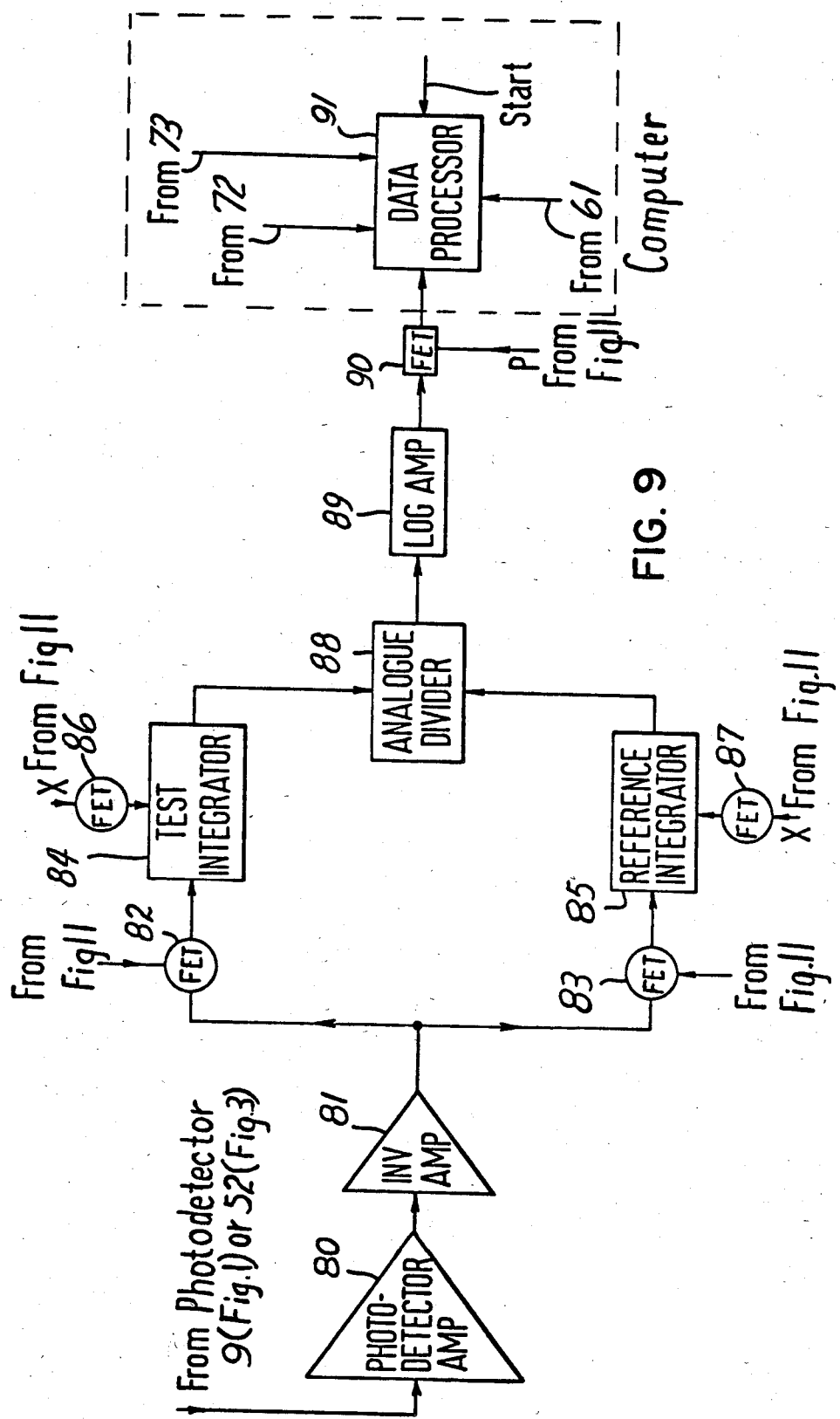
Figure 10:
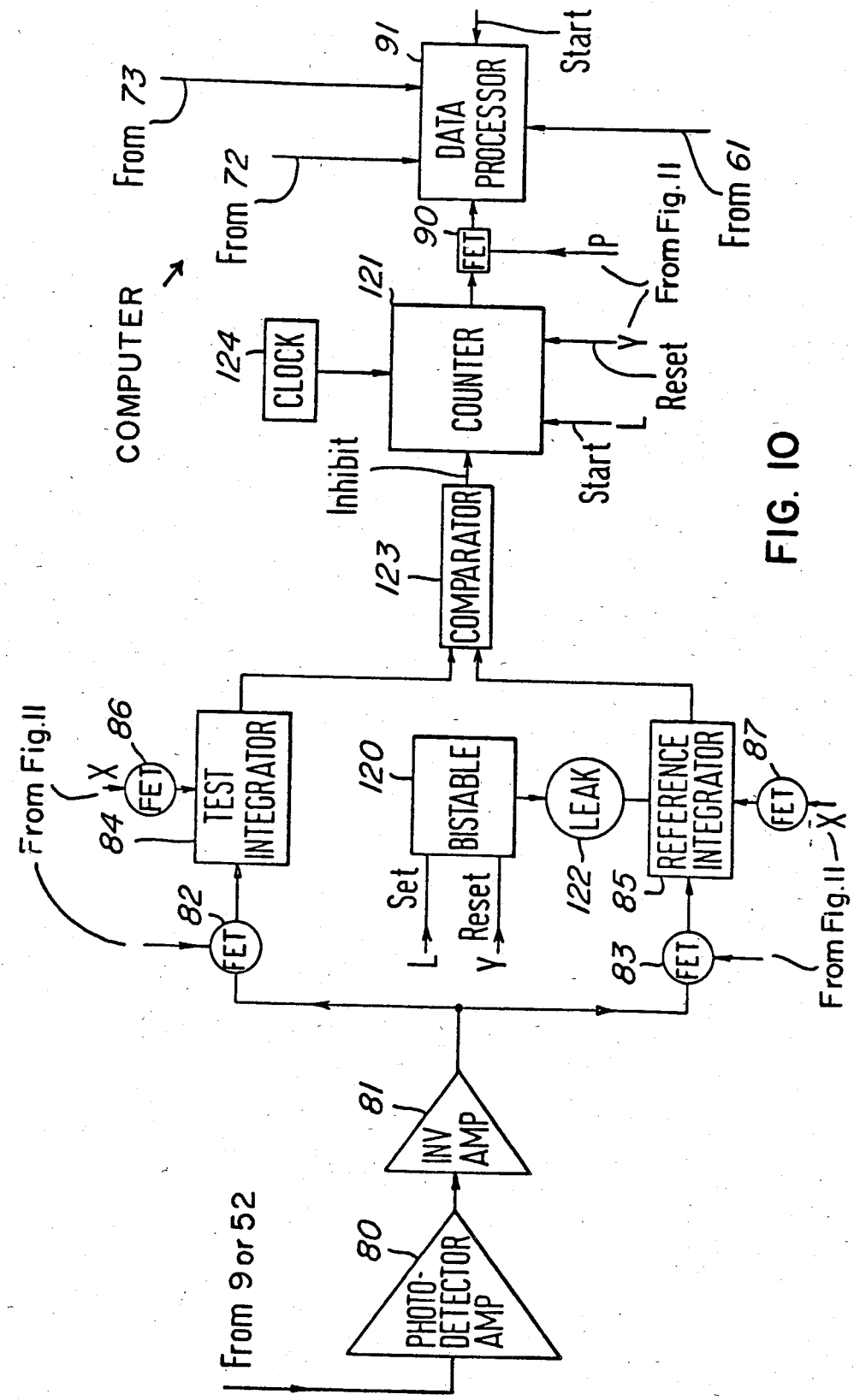
Figure 11:
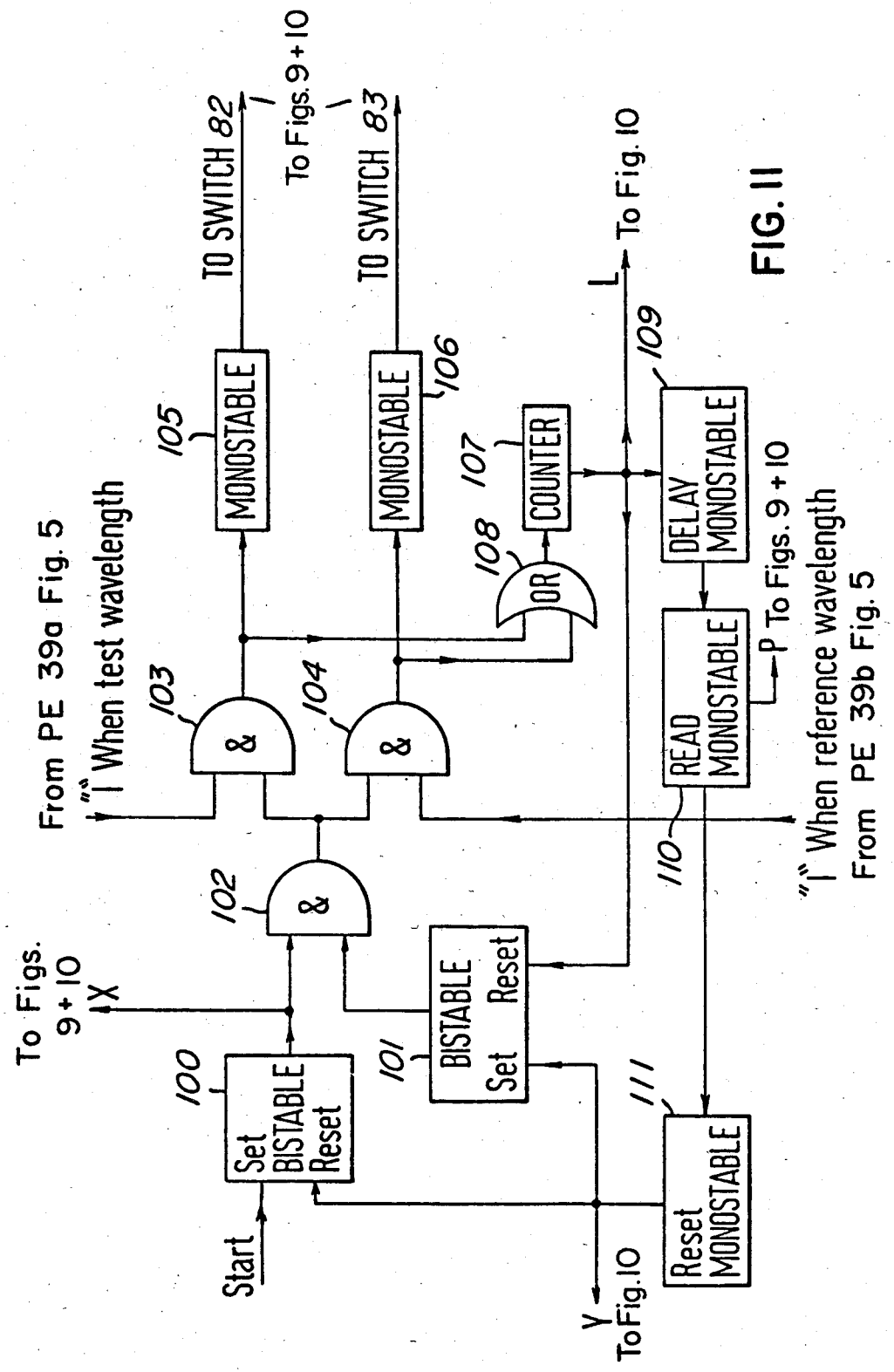

FIGS. 7 and 8 are a side elevation and a cross-section respectively of a tube in which part of the optical system of FIG. 6 is mounted; and FIGS. 9, 10 and 11 are diagrams of circuits associated with the devices of FIGS. 1 and 3.

The device shown in the accompanying drawings is for the monitoring of chemical reactions and analysing of chemical substances, and is particularly concerned with those reactions in which the specific absorbance at a particular wavelength of a sample to be analysed varies with time in the presence of a suitable reagent. The device to be described enables fresh samples to be prepared and placed in position for analysis in the device whilst previously prepared samples are undergoing analysis and accordingly allows a continuous throughput of samples to be analysed at a relatively rapid rate. The device includes a turntable rotatable about a vertical axis and carrying cuvettes for the samples to be analysed, the turntable being continuously slowly rotatable, or preferably indexable, through a series of angular positions (for example fifty in number), so that the cuvettes are moved or stepped so as to pass in sequence beneath appropriate means for loading them with samples and reagents. The monitoring is effected by scanning the loaded cuvettes repeatedly by a beam of light reflected outwardly from the axis of the turntable by a prism rotating much faster than the turntable, and the light is returned to the axis by mirrors to be detected by a photodetector such as a photomultiplier mounted on the turntable axis. After the monitoring the cuvettes are caused by the movement or indexing of the turntable to pass in sequence beneath means for emptying and cleaning the cuvettes before again passing the loading means. The loading, emptying and cleaning means are well known in the art and will not be described and are not shown in the drawings.

The device shown in FIG. 1 comprises a turntable 1 on which can be mounted two rows of cuvettes containing the samples to be analysed and which can be angularly stepped in the well known manner. Suitable known means may be provided to maintain the samples at a required temperature. Light is generated by a lamp 2 and directed by a mirror 3 down a rotatable tube 4. the tube 4 houses further prismatic mirrors 5 and 6. As the tube 4 rotates the mirror 5 directs light sequentially on to the two relatively staggered rows of cuvettes 7 so that the cuvettes are scanned by the light. At their backs the cuvettes have further mirrors 8 so that the light passing through the cuvettes is reflected back to the mirror 6 and via a lens system to a stationary photodetector 9. The tube 4 is rotated by an electric motor 10.

Thus by monitoring the output of the photodetector 9 the changes in the absorption of the contents of the cuvettes can be measured and stored for subsequent analysis.

Suitable openings are left in the turntable housing so that new cuvettes can be positioned on the turntable for testing, and old cuvettes removed. These loading and unloading stations are totally conventional and as such have not been fully described.

The device described has the advantage that analysis of the reaction can commence immediately the first cuvette has been loaded. Thus there is no long delay as in the previous device during which all the samples have to be placed in position on the rotor. The rate of rotation of the turntable can be selected so that the cuvettes can be monitored in rapid succession, for example at 5 millisecond intervals. The device described is particularly suitable for enzyme analysis. Suitable means may be provided on the periphery of the turntable 1 for cleaning the cuvettes.

However, in order to ascertain which cuvette is associated with a particular output from the photodetector 9 it is essential that the position of the tube 4 as it rotates should be continuously and accurately monitored. This is done by a shaft encoder comprising a light source 11 and a photodetector 12 separated by a series of apertures which move with the tube 4. Thus as the tube 4 rotates the photodetector 12 is illuminated as each aperture passes the light 11 so that its output is a series of pulses which can be stored in a counter 14 so that the reading in the counter is a measurement of the tube position and accordingly of the cuvette being scanned.

Figure 2:
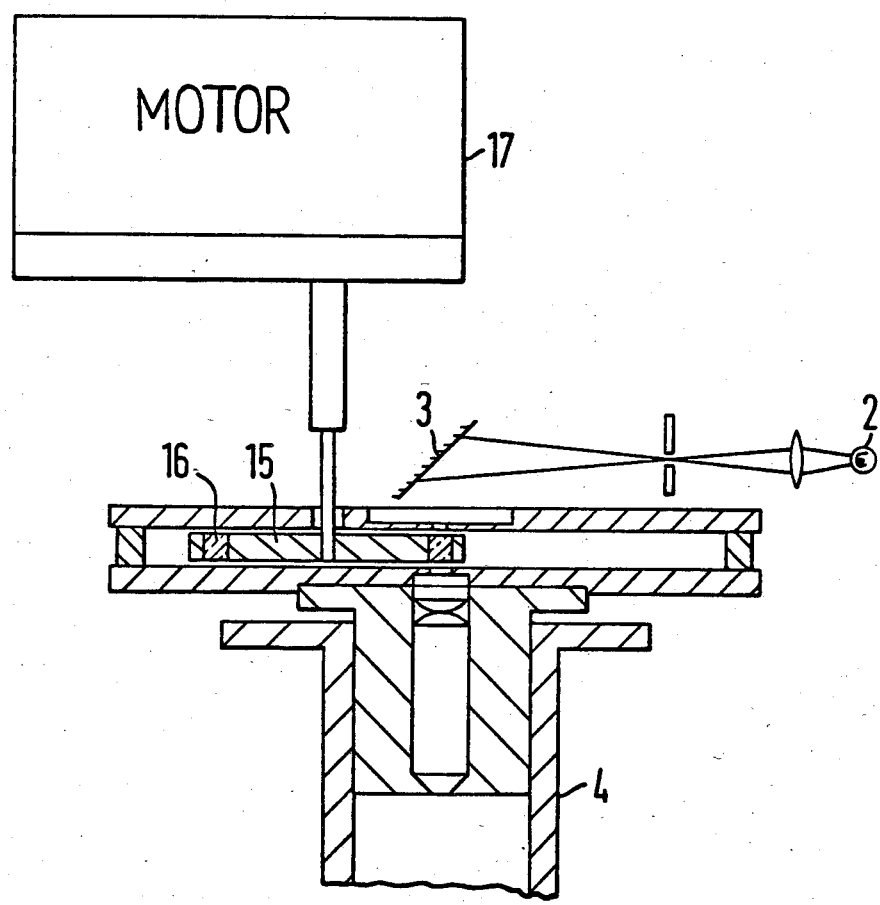

Furthermore, in order to normalise the output of the photodetector 9 so as to compensate for system drift and for non-specific absorbance in the biological samples, the absorption signals are measured at an active or test wavelength and then compared with signals measured at a reference wavelength. A number of these comparisons are therefore required as the beam of light scans each cuvette and this is achieved by chopping the light from the lamp into alternate wavelengths at a high frequency. Two possible methods may be used for this purpose and one of them is shown in FIG. 2 of the accompanying drawings. Thus FIG. 2 shows a disc 15 carrying at its periphery a plurality of interference filters 16 so that as the disc rotates an interference filter 16 interrupts the light path from the lamp 2. The disc 15 is rotated by a suitable electric motor 17.

In an alternative method a freely mounted disc carries only two filters and has turbine vanes mounted in its periphery. The disc is rotated at high speed by compressed air, again so as to chop the light from the lamp 2 into alternate frequencies.

It can thus be seen that the output of the photodetector rapidly alternates between two signals, namely one produced by light at the test or active wavelength and one at the reference wavelength. In order to obtain usable data it is accordingly necessary to process the output of the photodetector 9 so as to separate the active and reference signals so that they can be compared and to allocate the output signals to specific cuvettes. Before considering circuits for carrying out these functions, however, another more detailed embodiment of the FIG. 1 type structure is now described with reference initially to FIG. 3.

In FIG. 3, turntable 21 is machined from aluminium and has drilled in it one hundred cylindrical recesses 22 arranged in two concentric uniform circular arrays of fifty to allow a greater number of cuvettes to be carried for a particular diameter of turntable. This arrangement can best be seen in FIG. 4. Each recess 22 houses a cylindrical cuvette 23 (only one of which is shown in FIG. 3) for carrying a sample to be analysed. The recesses 22 of the two arrays are staggered relative to one another so that the light travelling outwardly from the turntable axis to the cuvettes in the outer row can pass through the spaces between the cuvettes in the inner row. The staggered arrangement also allows two separate reactions to be monitored if desired, one reaction in the cuvettes of the outer row, and one in the cuvettes in the inner row. The turntable 21 is mounted on ball race 24 in a cylindrical support 25 so that it can rotate freely. An electric motor 26 (subsequently referred to as the index motor) drives a rubber drive wheel 27 which firmly engages the outer periphery of the turntable 21 so that the turntable 21 can be indexed under the control of a control circuit to be described later. A cylindrical housing 28 is mounted on the upper side of the turntable 21 and carries a bichromator 29 for providing light of alternating wavelengths. The use of alternating wavelengths is to compensate for system drift and for non-specific absorbance in the samples. Thus one of the wavelengths is an active, or test, wavelength whilst the other is a reference wavelength chosen so that at this wavelength the absorbance does not vary as the relevant reaction proceeds; for a typical enzyme analysis, the active wavelength may be 340 nanometers and the reference wavelength may be 383 nanometers. The cuvettes 23 must of course be made of a material which is transparent at both wavelengths; for the specific wavelengths quoted a suitable material is quartz. The bichromator 29 is shown in greater detail in FIG. 5 and includes a lamp 30 and lens system 31 for providing a beam of light which falls on a beam splitter 32. The light reflected downwardly by the beam splitter 32 falls onto a prism 33 arranged to reflect the light falling on it into a direction parallel to the light transmitted through the beam splitter 32 so that two parallel upper and lower beams of light are produced. A cranked disc 34 rotatable by a suitable electric motor (not shown) about an axis 35 intercepts these two beams, with the two axially separated but parallel parts 34a and 34b of this disc respectively intercepting the two beams at their points of minimum diameter. Each disc part 34a and 34b has formed in it a circular array of equally spaced apertures 36 and 36' respectively, the number of apertures in each array being equal. As the apertures of the two arrays are relatively staggered, only aperture 36 of the inner array is not hidden in FIG. 5. When the disc 34 rotates, the upper and lower light beams are alternately interrupted because of the aperture staggering, the obstruction of one light beam coinciding with an aperture in the disc 34 allowing the passage of light in the other beam. In the present exemplary embodiment the disc 34 is rotated at 3000 r.p.m. and there are 20 apertures in each array. Each light beam is accordingly chopped at 1,000 cycles per second. The light passing through the apertures in the disc 34 is further collimated by lenses 37. The bichromator 29 is also provided with a pair of slots 38. The first slot 38 contains a slide apertured to allow the passage of light through it but carrying a pair of photodetectors 39a and 39b which respectively give output signals when the upper and lower beams of light pass respectively through apertures 36 and 36' of the disc 34. The purpose of this arrangement is described below. The second slot contains a slide 40 carrying a pair of filters 40a and 40b so as to produce light of differing wavelengths in the two beams, the wavelengths being of course the active or test wavelength and the reference wavelength.

After passing through its associated filter 40a the light in the upper beam falls on a reflecting prism 41 and is reflected onto a semi-reflecting device 42 where the two light beams are recombined to form a narrow collimated beam of light the wavelength of which will alternate between the active and reference wavelengths at a frequency dependent on the rate of rotation and number of apertures of the disc 34 as previously described, this beam being focussed by an objective lens 43.

The bichromator 29 is mounted on the housing 28 so that the alternating beam of light it produces passes along the axis about which the turntable 21 rotates through the aperture 44 into the optical system which is housed within the turntable 21 and which is shown in greater detail in FIG. 6.

The optical system shown in FIG. 6 comprises a lens doublet 45 and a prism 46 which reflects the light beam outwardly from the axis of rotation and inclined slightly downwardly towards the recesses 22 and their associated cuvettes 23. The light on passing through a cuvette 23 falls on a small concave spherical mirror 47 carried on a screw threaded plug 48 mounted within a radially extending screw threaded bore 49 in the turntable. The turntable is provided with one of these bores for each of the recesses 22 and two such bores are shown in the plan view of the turntable shown in FIG. 4. The mirror 47 reflects the light back through the cuvette 23 slightly downwardly and towards the axis of rotation, so that it falls on a further prism 50 which in turn reflects the light through a lens system 51 onto a photomultiplier 52 mounted coaxially with respect to the axis of rotation of the turntable 21; the lens system 51 and photomultiplier 52 are secured to the turntable 21. The positioning of the aperture 44, the prisms 46, 50 and the photomultiplier tube 52 on the axis of rotation of the turntable 21 has the advantage that by rotating the prisms 46, 50 in synchronism about the turntable axis and relative to any motion that the turntable itself may be undergoing, the cuvettes will be scanned sequentially by the light from the bichromator assembly 29 and only a single photomultiplier is needed to detect the light returned by the mirrors 47. The use of a cylindrical form for the cuvettes 23 is also advantageous, since by virtue of the focussing properties of this form of cuvette the photomultiplier 52 will receive light in respect of each cuvette over a larger fraction of each revolution of the scanning beam than would be the case if comparable cuvettes of flat-sided form were used. It will be appreciated that the precise optical path in respect of each cuvette 23 can be adjusted, to take account of slight differences between individual cuvettes, by rotating the relevant plug 48 in its bore 49 so as to effect movement of the corresponding mirror 47 in a radial sense with respect to the axis of the turntable 21.

In FIG. 6 only the central ray of the light beam is shown and it will be apreciated that it is impracticable to ensure that the focal point of the light beam is adjusted continually to accommodate the two different radii on which the mirrors 47 lie. Thus the lenses 45 are designed to focus the light beam onto a point equidistant between the two radii on which the mirrors 47 lie. The cavity within the turntable 21 is made only just large enough to permit the passage of the scanning light beam from the prism 46 to the prism 50 via the cuvettes 23 and mirrors 47, the beam passing within about one millimeter of the walls of this cavity, which are finished matt black to eliminate stray reflections.

In order to allow prisms 46, 50 to rotate together relative to the turntable 21 they are mounted in a brass tube 53 having a rectangular bore 54 in which the prisms 46, 50 are a sliding fit. The prisms are held in place by grub screws 55. This arrangement will be understood from FIGS. 3, 7 and 8. The tube 53 has a threaded collar 56 firmly screwed to a disc 57 in turn fastened to a cylindrical bearing tube 58 so that the latter rotates with the tube 53; the threaded coupling between the collar 56 and the disc 57 enables an accurate initial adjustment to be made of the vertical positioning of the prisms 46, 50 relative to the mirrors 47. The bearing tube has a pair of flanges 59, 60 which provide a seat for a shaft encoder 61 which is mounted rigidly with respect to the turntable 21. The shaft encoder 61 comprises a lamp 62 illuminating a disc 63 secured to the bearing tube 68 to rotate with the latter and having alternate opaque and translucent areas so that as the disc 63 rotates with the tube 68 a photocell 64 (fixed relative to the lamp 62) receives light of varying intensity so that the photocell output is an indication of the angular position of the tubes 53 and 58 and accordingly of which cuvette is being scanned by the light beam. In this embodiment the shaft encoder 61 gives 9,000 output pulses during a complete revolution of the tubes 53, 58.

Mounted at the upper end of the bearing tube 58 is a toothed gear 65 meshing with a gear wheel 66 carried on a shaft 67 extending vertically through a hole in the housing 28. The shaft 67 is driven by an electric motor 68 (subsequently referred to as the scanning motor). In the present embodiment the motor 68 rotates the tubes 53, 58, the lenses 45 and the prisms 46, 50 through 360° every two seconds (in a clockwise direction when viewed from above).

Figure 4:
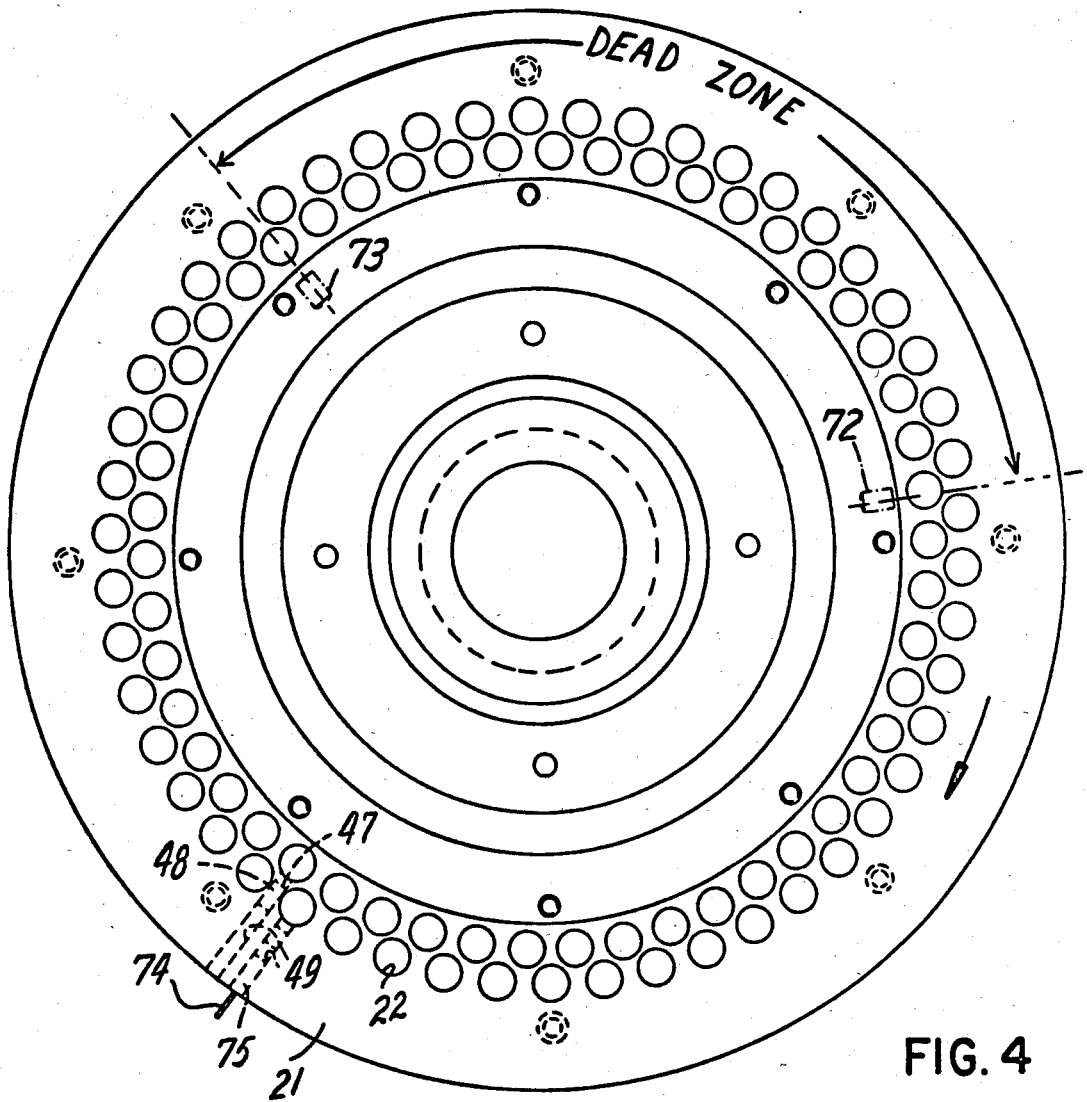
FIG. 4 is a plan view of part of the device shown in FIG. 3.

Also mounted on the bearing tube 58 is a cantilever arm 69 which is cranked so as to clear the gear wheel 66 and which carries at its outer end a lamp 70. The housing 28 is drilled with fifty evenly circumferentially spaced holes 71 and as the arm 69 rotates with the bearing tube 58 the lamp 70 is swept past the holes 71. A photocell 72 is mounted in a fixed position at the same vertical level as the holes 71, this position being chosen so that whenever the turntable 21 is in one of the angular positions through which it can be indexed, one of the holes 71 is opposite the photocell 72. The photocell 72 accordingly gives an output pulse every two seconds which is utilised in the control and data aquisition logic of the device. It will be appreciated that at any given time a sector of the turntable 21 is in a "dead" zone (FIG. 4); information cannot be derived from cuvettes in this zone because of the requirements of emptying, cleaning and loading the cuvettes while in the dead zone. Assuming turntable 21 rotates clockwise as shown in FIG. 4, the position of the photocell 72 defines the end of this dead zone. A second photocell 73 arranged similarly to the photocell 72 defines the start of this dead zone; the photocell 73 cannot be seen in FIG. 3 because the dead zone subtends an angle of less than 180° at the circumference of the turntable 21, the positions of photocells 72 and 73 being indicated in FIG. 4. While it was above assumed that turntable 21 rotates in the same direction (clockwise when viewed from above) as tubes 53, 58, lenses 45 and prisms 46, 50, turntable 21 can as well rotate in the opposite direction in which case the dead zone starting and ending roles of photocells 72, 73 would be reversed.

The basic principles of operation of the device being described have already mentioned; that is rapid rotation of the cuvette scanning beam as compared to relatively slow continuous movement or indexing of the turntable through the monitoring or non-dead zone and into the dead zone past devices for emptying, cleaning and loading the cuvettes with the light being detected by a single photomultiplier after its passage through the cuvettes in the monitoring zone.

The actual indexing of the turntable 21 is controlled by a series of fifty vanes 74 mounted on plugs 75 inserted into those bores 49 corresponding to the outer array of cuvettes 23 so that a vane 74 (only one of which is shown in FIG. 3) extends from the periphery of the turntable 21 in register with each cuvette 23 of the outer array.

As the turntable 21 rotates the vanes 74 successively pass between a pair of arms 76, the upper arm carrying a small lamp 77 and a lower arm a photocell 78 so that the presence of a vane 74 between the arms 76 obstructs the light to the photocell 78. The purpose of this latter arrangement is to define, as explained below, the amount of rotation of the turntable 21 for each step of its motion.

One facet which is of considerable importance is the identification of a particular portion of the output signal of the photomultiplier 52 with a particular sample, and in the following portion of this description the interrelationship between the indexing of the turntable 21 by the index motor 26, the outputs of the shaft encoder 61 and the photocells 72, 73 and 78, and a data processor (described below) for interpreting the data from the photomultiplier 52 will be described together with the sequence of operation of the device.

Let it be assumed that all the cuvettes on the turntable are empty and that the means for emptying, cleaning and loading the cuvettes are ready for operation as the turntable 21 indexes. The motor driving the bichromator disc 34 and the scanning motor 68 are started, and the lamps 30, 62, 70 and 77 switched on. Thus, while turntable 21 is initially resting in one of the angular positions from which it is to be indexed to the next, arm 69 carrying lamp 70 rotates with the optical system causing photocells 72 and 73 to give a respective output pulse once every complete revolution of the optical system. The output pulses of the photocell 73 are counted in a counter forming part of a control circuit 79, and after the occurrence of the sixth pulse (using six as an exemplary number of times the optical system rotates 360° while the turntable rests in an indexed position) the index motor 26 is started by a signal from this counter. The turntable 21 is then rotated, preferably but not necessarily in the same sense as tubes 53, 58, until a vane 74 obstructs the light to the photocell 78 at which point the change in output of the photocell 78 causes the circuit 79 to stop the index motor 26, this rotation thus corresponding to one fiftieth of a complete revolution of the turntable 21.

The indexing of the turntable 21 from its start position brings a first pair of cuvettes (one from each of the inner and outer arrays) out of the dead zone and the output pulse from the photocell 72 immediately following the sixth pulse from the photocell 73, i.e., the sixth or seventh output pulse from photocell 72 according to whether the optical system started from a position in the non-dead zone or dead zone respectively, "enables" the data processor to accept the information produced by the output of the photomultiplier 52. Accordingly, the outputs of the photomultiplier 52 caused by the light sequentially passing through the cuvettes of this first pair to emerge from the dead zone is the first piece of relevant data to reach the data processor. The data processor labels this data as being derived from the first and second samples. It is of course necessary to ensure that whenever these particular samples are scanned by the light beam the resulting outputs from the photomultiplier 52 are always attributed to them, and similarly for the subsequent pairs of cuvettes which emerge in succession from the dead zone.

This is achieved as follows. The circuit 79 counts the output pulses from photocell 73 and restarts the index motor 26 after every six revolutions of the optical system so that the turntable 21 is indexed by a similar amount every twelve seconds. Thus the turntable 21 is advanced every twelve seconds to bring a fresh pair of cuvettes and their newly loaded samples out of the dead zone, the control circuit 79 being arranged so that the movement of the turntable 21 occurs while the beam of light is scanning cuvettes 23 located in the dead zone. Each output of the photocell 72, once operation of the device has started, is an indication that the scanning beam of light has left the dead zone and has entered the monitoring region, so that the data produced from the output of photomultiplier 52 is to be processed in the data processor. Similarly, each output from the photocell 73 marking the beginning of the dead zone informs the data processor that the data from the photomultiplier 52 is of no value and that the sole function of the data processor in respect of data acquisition is then to store the output of the shaft encoder 61 to ensure that every cuvette is kept track of. The output from the shaft encoder 61 is stored in a counter in the data processor so that this stored value is a constantly updated record of the position of the scanning beam of light. Every 90th pulse from the shaft encoder 61 will indicate that the scanning beam has passed into a new section corresponding to one cuvette, so that the data processor can assign any output from the photomultiplier 52 during the period corresponding to the next 90 pulses to the relevant cuvette, and hence (in conjunction with a count of the pulses from the photocell 73) to the relevant sample.

It will be appreciated that the indexing of the turntable 21 gives rise to no problem in respect of the allocation of the data, since the shaft encoder 61 itself is indexed with the turntable 21.

A further complication in the data processing is introduced by the need to scan each sample at both test and reference wavelengths for reasons which have been given previously. Thus the output from photomultiplier 52 alternates rapidly between two values a number of times even during the short period of time for which the light beam scans a single sample. Due to the fact that the light beam is reflected from each cuvette except over a very narrow range of angles of incidence, the period over which data can be obtained from a single cuvette during a single scan is in the order of 5 milliseconds; it will be appreciated that the light scanning the cuvette during this period will alternate several times between the test and reference wavelengths. It is accordingly necessary to process the output of the photomultiplier 52 so as to separate the active and reference signals so that they can be compared, as well as to allocate the output signals to specific samples.

FIGS. 9, 10 and 11 show circuits for carrying out some of these functions, and are applicable to either the FIG. 1 or FIG. 3 embodiment. The circuit of FIG. 9 is suitable for systems where an analogue output is required, FIG. 10 is a similar circuit for giving a digital output, and FIG. 11 is a logic control circuit for controlling the circuits of either FIG. 9 or FIG. 10.

The data processing circuit of FIG. 9 comprises an F.E.T. input operational amplifier 80 connected to the output of the photodector 9 of FIG. 1 or the photomultiplier 52 of FIG. 3, and which produces an output voltage proportional to the output signal from the photodetector 9 or photomultiplier 52. An inverting amplifier 81 inverts the output of the amplifier 80 to provide the correct polarity and feeds two parallel branches containing respectively switching F.E.T's 82, 83 which are turned on alternately by the logic control circuit of FIG. 11 (in a manner described later in the specification) in order to ensure that the active and reference signals from the photodetector 9 or photomultiplier 52 are appropriately routed to one of a pair of integrators 84, 85. Integrator 84 is for integrating that portion of the output of photodetector 9 or photomultiplier 52 caused by the active wavelength, and integrator 85 for integrating the portion caused by the reference wavelength. A pair of F.E.T. clamps 88, 87 are respectively connected across the integrators 84, 85 for resetting the integrators to zero after the resultant of the signals from the integrators has been sampled or read as described below. Both clamps 88, 87 are controlled by the X signal output from FIG. 11, and are normally maintained "ON" by a logic zero, thus ensuring that the integrators 84, 85 are prevented from drifting, and are only switched "OFF" just before the integrator sampling or reading takes place. The outputs of the integrators 84, 85 are taken to an analogue divider 88 which gives an output voltage proportional to the ratio of the output voltages of the two integrators, and this output voltage is taken to an analogue logarithmic amplifier 89, the output of which gives a linear indication of optical density. An F.E.T. switch 90 controlled by a P signal input from the logic circuit of FIG. 11 is provided to couple the output of amplifier 89 to a computer including data processor 91 so that the output of amplifier 89 can be assigned to an appropriate sample, for example in response to the output signals of the shaft encoder 61 and photocell 73 as previously described in connection with the FIG. 3 embodiment.

Figure 5:
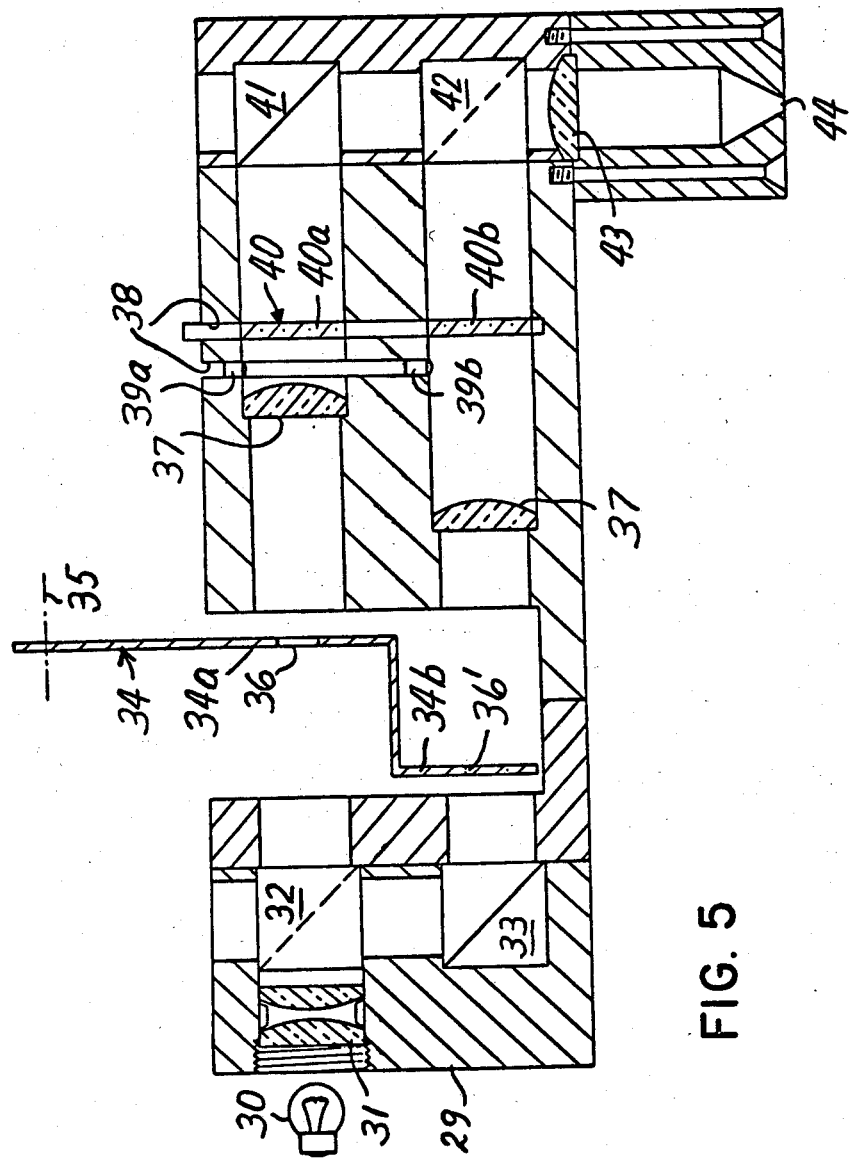
FIG. 5 is a section through a bichromator forming part of the device shown in FIG. 3.

The circuit of FIG. 11 which is capable of controlling either of the signal processing circuits of FIGS. 9 and 10 comprises an edge triggered bistable circuit 100. The pulses derived from the shaft encoder 11-13 of FIG. 1 and stored in counter 14, or the shaft encoder 61 of FIG. 3 and stored in the relevant counter in the FIG. 9 data processor 91, both as previously described, produce a command pulse when the light beam is in the correct position on each cuvette; for example, in keeping with the exemplary 9000 pulses from encoder 61 per revolution and 100 cuvettes total, a command pulse is produced on every 90th pulse from the shaft encoder 61. This command signal is labeled "start" in FIG. 11 and is applied to one input of the bistable circuit 100 so that on receipt of the command pulse the output of the bistable 100 is set to logic 1 so as to perform two functions. Firstly, it switches off the integrator clamp F.E.T's 86, 87 of FIG. 9 so as to enable the two integrators 84, 85 and secondly, in conjunction with a further bistable 81 it opens an AND gate 102. The transition of the output of gate 102 from logic zero to logic 1 enables two further AND gates 103 and 104. The AND gates 103, 104 are operated alternately by pulses derived from disc 15 in FIG. 2 by a suitable, simple photosensitive or relay system, and in FIG. 5 the pulses are derived from the photocells 39a and 39b of the bichromator 29 in accordance with the rate at which the two light beams in the bichromator are interrupted by the disc 34, so that AND gate 103 is opened with a "1" pulse (from photocell 39a for example) when a cuvette is being scanned with the test wavelength and AND gate 104 is opened with a "1" pulse (from the other photocell 39b) when a cuvette is being scanned with the reference wavelength. The outputs of the AND gates 103, 104 are used to trigger a pair of monostables 105, 106, which in turn are coupled to switches 82, 83 of FIG. 9, thus permitting the related integrators 84, 85 to sample the output of the inverting amplifier 81 for periods determined by the on times of the monostables 105, 106. This eliminates the need for absolute uniformity of speed of the filter disc 15 (FIG. 2) or the bichromator disc 34 (FIG. 5). The outputs of the gates 103, 104 are also taken to a counter 107 via an OR gate 108. The counter 107, which may be an up/down counter, is arranged to count an even number "N" of pulses before producing one output pulse and resetting itself. "N" may for example be six thus permitting three samples of the output of the photodetector photomultiplier 52 for each wavelength to be integrated. The output of the counter 107 is taken to the bistable 101 so that on receipt of a pulse from the counter 107 the output of the bistable 101 goes to logic zero thus inhibiting the AND gate 102 which in turn inhibits the AND gates 103, 104 so as to prevent the integrators 84, 85 from taking any more samples. A standard delay monostable 109 also receives the output pulse from the counter 107 and provides a delay suitable to allow the outputs of the analogue divider 88 and logarithmic amplifier 89 of FIG. 9 to settle before the output of the amplifier is read into the data processor 91. This operation is performed by a read monostable 110 the output P of which controls the read switch 90 in FIG. 9. Finally, the output of the read monostable 110 is taken to a reset monostable 111 which is used to reset the circuit prior to commencement of the next cycle of operations. The reset monostable 111 is triggered by the trailing edge of the monostable 110 and performs the following functions:

1. Sets output of bistable 101 to logic "1".
2. Simultaneously resets the output of bistable 100 to logic zero which in turn switches on the integrator reset and clamp F.E.T's 86, 87 so as to reset the integrators 84, 85.

When the circuit of FIG. 10 is used in place of that of FIG. 9, the reset monostable 111 also performs the further functions:

3. Resets a bistable 120 which forms part of the circuit of FIG. 10.
4. Resets to zero a counter 121 which also forms part of the circuit FIG. 10.

The circuit of FIG. 10 is partly the same as that of FIG. 9, and accordingly integers common to both circuits have been given the same reference numerals. The operation of these integers is controlled in a similar manner to that described above. However, FIG. 10 also includes a bistable 120 which is switched to logic "1" on receipt of an output pulse from counter 107 in the circuit of FIG. 11, and a counter 121 which is started by the output pulse L from counter 107 in FIG. 11. An F.E.T. switch 122 in FIG. 10 is connected across the reference integrator 85 and the logic "1" signal from bistable 120 turns on switch 122 to allow the integrating capacitor of integrator 85 to discharge. It is a requisite of the system described that the output voltage from integrator 85 will always be higher than that from integrator 84. Thus the discharge time constant must be fast enough to permit the voltage output of integrator 85 to decay down to the value of the output voltage from integrator 84 well before the next cuvette is to be monitored.

The outputs of the integrators 84, 85 are taken to a precision comparator 123 which monitors the output voltages of both integrators. When the output voltage of integrator 85 falls below that of integrator 84 the output polarity of comparator 123 reverses and inhibits counter 121. The counter is driven, when not inhibited, by a crystal clock 124. Thus when the counter 121 is started by a signal L from the counter 107 in the FIG. 11 control circuit it continues to count until an inhibit signal is received from comparator 123. The count stored in the counter 121 will then be a linear function of the optical density of the sample in the cuvette being scanned. Therefore, for a given cuvette the count difference between consecutive scans is a function of the normalised optical density change. The count stored in the counter 121 is read into the data processor 91 by the read switch 90 on a command signal P from the "read" monostable 110 of FIG. 11.

As previously described, the reset monostable 111 is triggered by the trailing edge of the "read" monostable 110 and resets bistable 120, thus removing the resistive leak across integrator 85, and resets counter 121 to zero.

It will be appreciated that with the system described above the optical density indication obtained for each cuvette on each scan is effectively derived by averaging several readings at each of the test and reference wavelengths. This has the advantage of enabling accurate results to be achieved without imposing such a high standard of mechanical precision in the construction of the apparatus as would be required if only a single reading was taken at each of these wavelengths for each cuvette.

It will be appreciated that the embodiment described above enables the reaction involving a particular sample to be monitored at intervals of two seconds over a period of greater than five minutes, and that the device is capable of handling throughput of up to 600 samples per hour.

While the embodiments of FIGS. 1 and 3 have generally been described with means for indexing the turntable, i.e., with a stop and go action with the monitoring effectively occurring while the turntable is stopped, it is also possible within the scope of this invention to effect the monitoring scans while the turntable is continuously moved at a slow pace, as one of ordinary skill in the art will appreciate in view of the speed of light and electronics involved. Hence, means for repeatedly rotating the turntable as used in the claims is meant to be generic to indexing and continuous movement of the turntable. Other variations and modifications of the described embodiments will become apparent to those skilled in the art and such are to be considered as part of this invention to the degree they are covered by the scope of the following claims including equivalents of the disclosed embodiments.

We claim:

1. Apparatus for monitoring chemical reactions occurring in a plurality of liquid or the like sample substances carried in a plurality of respective cuvettes whose walls are at least to some extent capable of transmitting radiant energy which comprises:

support means, a sample loading station having sample loading means mounted on said support means, a sample unloading station having sample unloading means mounted on said support means, a sample carrier on said support means for mounting a plurality of samples in radiation-transmissive cuvettes, said cuvettes being disposed serially in a line on said carrier, photometer means on said support means for producing at least one beam of radiation arranged to intersect said line so as to traverse each cuvette which may move relative to said beam, said photometer means including means to detect the radiation resulting from the said traversal, means for moving both the carrier and the photometer means to cause said beam consecutively to traverse said cuvettes and any samples which may be contained therein, the carrier being constructed and arranged continuously to move said cuvettes in a closed, looped path and by stepping action past the sample loading station and the sample unloading station whereat said sample loading and unloading means respectively load and unload samples into and from different cuvettes, the relative movement being in accordance with a continuous program that for each cuvette of said carrier loads a sample, passes the sample along said path while said photometer means beam intersects and traverses the sample a plurality of times and unloads the said sample, and means responsive to the traversed, detected radiation to provide a measure of radiation absorbence by each said sample for each traversal thereof by said beam.

2. An automatic chemistry machine comprising:

a rotatable carrier for conveying a multiplicity of samples to be examined, means at a loading station for loading samples on the carrier and means at an unloading station for unloading samples moved by the carrier from the loading station to the unloading station, photometric means for photometric examination of samples in transit between the loading and unloading stations, and means for causing a plurality of passages of each sample past the photometric means in transit between the loading and unloading stations including drive means for rotating both the carrier and photometric means.

3. In a method for examining the chemical reactions of a multiplicity of samples, the improvement comprising the steps of:

carrying said multiplicity of samples on a movable carrier in a closed loop path, loading said samples on the carrier at a loading station, unloading said samples at an unloading station after the samples have been moved by the carrier from the loading station to the unloading station, moving both said carrier and a photometric means including effectively passing each sample past the photometric means a plurality of times while in transit in said path between the loading and unloading stations, and photometrically examining the samples during their said plural passes of the photometric means before the said unloading of the samples at said loading station.

4. A method as in claim 3 wherein said loading and unloading of said samples comprises a continuous throughput of said samples via said carrier.

5. An apparatus for use in the analysis of a series of samples, comprising:

a turntable having a multiplicity of positions at which separate samples can be carried, said positions being arranged in a circular array centred on the rotational axis of the turntable, loading means for introducing samples sequentially on to the turntable at a first location, unloading means for removing samples sequentially from the turntable at a second location, the loading and unloading means being recurrently operable with the same recurrence frequency, a photometric system for the photometric examination of samples carried by the turntable at said positions, and drive means for causing relative rotation of the turntable and at least part of the photometric system, the drive means being operative to effect repetitive rotary movements of the turntable such that each of said positions will in turn, in a repeated predetermined sequence of the positions, initially be disposed at said first location at a time when the loading means is operable to introduce a sample and subsequently be disposed at said second location at a time when the unloading means is operable to remove a sample, the interval between said two times in respect of each of said positions being sufficiently long to ensure that by virtue of said relative rotation each sample introduced on to the turntable by the operation of the loading means will be subjected to plurality of successive examinations by the photometric system before that sample is removed from the turntable by the operation of the unloading means.

* * * * *